(12) United States Patent
Zhu

(10) Patent No.: US 8,816,120 B2
(45) Date of Patent: Aug. 26, 2014

(54) **PROCESS FOR THE PREPARATION OF *N*-(4-NITRO-2-SULFAMOYL-PHENYL)-MALONAMIC ACID METHYL ESTER AND *N*-(4-AMINO-2-SULFAMOYL-PHENYL)-MALONAMIC ACID METHYL ESTER**

(71) Applicant: Hoffmann-La Roche Inc., Nutley, NJ (US)

(72) Inventor: Jiang Zhu, Wayne, NJ (US)

(73) Assignee: Hoffmann-La Roche Inc., South San Francisco, CA (US)

( * ) Notice: Subject to any disclaimer, the term of this patent is extended or adjusted under 35 U.S.C. 154(b) by 0 days.

(21) Appl. No.: 14/153,878

(22) Filed: Jan. 13, 2014

(65) Prior Publication Data

US 2014/0200362 A1 Jul. 17, 2014

Related U.S. Application Data

(60) Provisional application No. 61/751,999, filed on Jan. 14, 2013.

(51) Int. Cl.
*C07C 315/00* (2006.01)
(52) U.S. Cl.
USPC ............................................................ 560/13

(58) Field of Classification Search
None
See application file for complete search history.

(56) References Cited

U.S. PATENT DOCUMENTS

| 7,939,524 B2 | 5/2011 | Tran et al. |
| 8,101,800 B2 | 1/2012 | Tran et al. |
| 8,236,948 B2 | 8/2012 | Tran et al. |
| 8,546,602 B2 | 10/2013 | Tran et al. |

FOREIGN PATENT DOCUMENTS

WO WO2010/042834 4/2010

*Primary Examiner* — Brandon Fetterolf
*Assistant Examiner* — Ana Z Muresan
(74) *Attorney, Agent, or Firm* — Womble Carlyle Sandridge & Rice

(57) ABSTRACT

The present invention provides a novel method for preparing compounds N-(4-nitro-2-sulfamoyl-phenyl)-malonamic acid methyl ester and N-(4-amino-2-sulfamoyl-phenyl)-malonamic acid methyl ester, which are novel intermediates for preparing a key intermediate N-(4-methanesulfonylamino-2-sulfamoyl-phenyl)-malonamic acid methyl ester, for the preparation of N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1$\lambda^6$,2,4-benzothiadiazin-7-yl) methanesulfonamide, also known commercially as Setrobuvir, a compound useful in treating hepatitis C.

7 Claims, No Drawings

PROCESS FOR THE PREPARATION OF N-(4-NITRO-2-SULFAMOYL-PHENYL)-MALONAMIC ACID METHYL ESTER AND N-(4-AMINO-2-SULFAMOYL-PHENYL)-MALONAMIC ACID METHYL ESTER

CROSS-REFERENCE TO RELATED APPLICATIONS

This application claims priority benefit of U.S. Provisional Patent Application Ser. No. 61/751,999, filed Jan. 14, 2013, which is hereby incorporated by reference in its entirety.

FIELD OF THE INVENTION

The present invention provides a novel method for preparing compounds N-(4-nitro-2-sulfamoyl-phenyl)-malonamic acid methyl ester and N-(4-amino-2-sulfamoyl-phenyl)-malonamic acid methyl ester, which are novel intermediates for preparing a key intermediate N-(4-methanesulfonylamino-2-sulfamoyl-phenyl)-malonamic acid methyl ester, for the preparation of N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1λ$^6$,2,4-benzothiadiazin-7-yl)methanesulfonamide, also known commercially as Setrobuvir, a compound useful in treating hepatitis C.

The present invention also relates to novel intermediate compounds useful for the preparation of Setrobuvir, specifically N-(4-nitro-2-sulfamoyl-phenyl)-malonamic acid methyl ester and N-(4-amino-2-sulfamoyl-phenyl)-malonamic acid methyl ester.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

Setrobuvir, a 5,6-dihydro-1H-pyridin-2-one compound, specifically N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1λ$^6$,2,4-benzothiadiazin-7-yl)methanesulfonamide (U.S. Pat. No. 7,939,524, herein expressly incorporated by reference) is one of the compounds useful in treating HCV. U.S. Pat. No. 7,939,524 and WO 2010/42834 both disclose Setrobuvir as well as method(s) of making same.

A key intermediate in the preparation of Setrobuvir is N-(4-methanesulfonylamino-2-sulfamoyl-phenyl)-malonamic acid methyl ester. A number of methods of making this intermediate in the preparation of Setrobuvir have been noted in U.S. Pat. No. 7,939,524, and WO 2010/42834, but these routes have some drawbacks. Fox example, in WO2010/42834, the production of the electron-rich diaminobenzene intermediate 2,5-diamino-benzenesulfonamide is prone to color-generation issues that need to be reduced in the next intermediate, or it can result in color issues in the final product (Setrobuvir). Additionally, the WO2010/42834 route can also result in a chloro impurity (identified via LC/MS in the key intermediate N-(4-methanesulfonylamino-2-sulfamoyl-phenyl)-malonamic acid methyl ester.

Accordingly, a novel method for preparing Setrobuvir via the key intermediate N-(4-methanesulfonylamino-2-sulfamoyl-phenyl)-malonamic acid methyl ester is required to avoid the production of the electron rich diaminobenzene intermediate, and possible color issues in Setrobuvir, as well as to eliminate the chloro impurity in the key intermediate N-(4-methanesulfonylamino-2-sulfamoyl-phenyl)-malonamic acid methyl ester.

SUMMARY OF THE INVENTION

The present invention describes a method for making the intermediate compound N-(4-methanesulfonylamino-2-sulfamoyl-phenyl)-malonamic acid methyl ester, which is used in the preparation of Setrobuvir, as well as novel intermediate compounds useful for the production of the key intermediate N-(4-methanesulfonylamino-2-sulfamoyl-phenyl)-malonamic acid methyl ester.

The present invention thus provides a method for the preparation of the intermediate compound N-(4-methanesulfonylamino-2-sulfamoyl-phenyl)-malonamic acid methyl ester, wherein

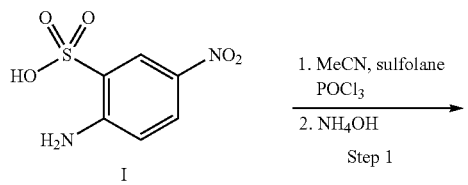

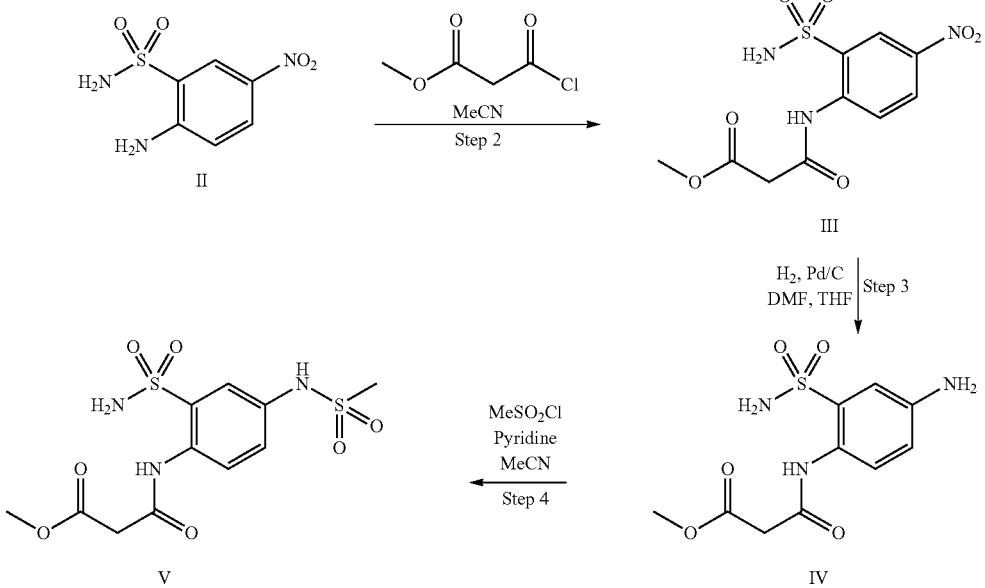

The present invention also provides novel intermediate compounds for the preparation of the intermediate compound N-(4-methanesulfonylamino-2-sulfamoyl-phenyl)-malonamic acid methyl ester (V), wherein the two novel intermediate compounds are N-(4-nitro-2-sulfamoyl-phenyl)-malonamic acid methyl ester (III) and N-(4-amino-2-sulfamoyl-phenyl)-malonamic acid methyl ester (IV).

The present invention further provides a method for the preparation of the intermediate compound N-(4-methanesulfonylamino-2-sulfamoyl-phenyl)-malonamic acid methyl ester (V) which comprises
a. reacting 2-amino-5-nitrobenzenesulfonic acid (I) with phosphorus oxychloride and then aqueous ammonia to form 2-amino-5-nitrobenzenesulfonamide (II)
b. adding methyl 3-choloro-3-oxypropanoate to 2-amino-5-nitrobenzenesulfonamide (II), in the absence of any base, to form N-(4-nitro-2-sulfamoyl-phenyl)-malonamic acid methyl ester (III),
c. reducing the N-(4-nitro-2-sulfamoyl-phenyl)-malonamic acid methyl ester (III), via a catalyst in the presence of an polar aprotic solvent or a polar aprotic solvent mixture, to form N-(4-amino-2-sulfamoyl-phenyl)-malonamic acid methyl ester (IV), and
d. mesylating the N-(4-amino-2-sulfamoyl-phenyl)-malonamic acid methyl ester (IV), via addition of methanesulfonyl chloride to a suspension of N-(4-amino-2-sulfamoyl-phenyl)-malonamic acid methyl ester (IV) and pyridine to form the intermediate compound N-(4-methanesulfonylamino-2-sulfamoyl-phenyl)-malonamic acid methyl ester (V).

The present invention further additionally provides a method of preparing the intermediate compound N-(4-methanesulfonylamino-2-sulfamoyl-phenyl)-malonamic acid methyl ester (V) comprising
a. reacting 2-amino-5-nitrobenzenesulfonic acid (I) with phosphorus oxychloride and then aqueous ammonia to form 2-amino-5-nitrobenzenesulfonamide (II)
b. adding methyl 3-choloro-3-oxypropanoate to 2-amino-5-nitrobenzenesulfonamide (II), in the absence of any base, to form N-(4-nitro-2-sulfamoyl-phenyl)-malonamic acid methyl ester (III),
c. reducing the N-(4-nitro-2-sulfamoyl-phenyl)-malonamic acid methyl ester (III), via a catalyst in the presence of an polar aprotic solvent or polar aprotic solvent mixture, to form N-(4-amino-2-sulfamoyl-phenyl)-malonamic acid methyl ester (IV), wherein the aprotic solvent is selected from the group consisting of DMF, DMA, THF, NMP or solvent mixtures thereof, and is more preferably a solvent mixture, and
d. mesylating the N-(4-amino-2-sulfamoyl-phenyl)-malonamic acid methyl ester (IV), via addition of methanesulfonyl chloride to a suspension of N-(4-amino-2-sulfamoyl-phenyl)-malonamic acid methyl ester (IV) and pyridine to form the intermediate compound N-(4-methanesulfonylamino-2-sulfamoyl-phenyl)-malonamic acid methyl ester (V).

DETAILED DESCRIPTION OF THE INVENTION

The present invention relates to a novel preparation method for the intermediate compound N-(4-methanesulfonylamino-2-sulfamoyl-phenyl)-malonamic acid methyl ester (V), which is used in the preparation of N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1$\lambda^6$,2,4-benzothiadiazin-7-yl)methanesulfonamide, also known commercially as Setrobuvir, a compound useful in treating hepatitis C. The present invention also relates to novel intermediate compounds useful for the preparation of the intermediate compound N-(4-methanesulfonylamino-2-sulfamoyl-phenyl)-malonamic acid methyl ester (V), specifically N-(4-nitro-2-sulfamoyl-phenyl)-malonamic acid methyl ester (III) and N-(4-amino-2-sulfamoyl-phenyl)-malonamic acid methyl ester (IV).

There are two major advantages for the novel method of the present invention over the routes described in U.S. Pat. No. 7,939,524 and WO 2010/42834. The first advantage is that the new route avoids the diaminobenzene intermediate (WO 2010/42834 Original Synthetic Route, compound VII). This electron rich intermediate is prone to color generation which has to be reduced at the next intermediate or it can cause color issues in Setrobuvir. The second advantage is that the new route eliminates a chloro impurity that has been detected by LC/MS in the intermediate compound N-(4-methanesulfonylamino-2-sulfamoyl-phenyl)-malonamic acid methyl ester as prepared by the routes described in WO 2010/42834.

DEFINITIONS

As used herein, the following terms have the given meanings:

The term "catalytic amount", as used herein, refers to that amount of catalyst necessary to promote a chemical reaction. Although a catalyst undergoes no chemical change, it is often physically changed by the chemical reactants. The exact amount of catalyst necessary to promote a chemical reaction varies by the type of catalyst as well as the reactants employed and is readily determined by one skilled in the art.

The phrase "in the absence of an additional base" means absence of any additional organic or inorganic compound, capable of accepting a proton.

The term "polar aprotic solvent" refers to a solvent that preferably has a large dielectric constant (>20) and a large dipole moment, but does not participate in hydrogen bonding. Representative and preferred examples of polar aprotic solvent include dimethylformamide (DMF), dimethylacetamide (DMA), tetrahydrofuran (THF), N-methylpyrolidone (NMP) or solvent mixtures thereof (polar aprotic solvent mixture).

methanesulfonamide, also known commercially as Setrobuvir, a compound useful in treating hepatitis C. The present invention also relates to novel intermediate compounds useful for the preparation of the key intermediate N-(4-methanesulfonylamino-2-sulfamoyl-phenyl)-malonamic acid methyl ester (V), specifically N-(4-nitro-2-sulfamoyl-phenyl)-malonamic acid methyl ester (III) and N-(4-amino-2-sulfamoyl-phenyl)-malonamic acid methyl ester (IV).

In U.S. Pat. No. 7,939,524 and WO 2010/42834, the compound N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1λ$^6$,2,4-benzothiadiazin-7-yl) methanesulfonamide, also known commercially as Setrobuvir, is disclosed, as well as methods of making same via the key intermediate N-(4-methanesulfonylamino-2-sulfamoyl-phenyl)-malonamic acid methyl ester (V). A disclosed method of synthesizing the key intermediate N-(4-methanesulfonylamino-2-sulfamoyl-phenyl)-malonamic acid methyl ester, as disclosed by WO 2010/42834, is the following:

Synthesis of N-(4-Methanesulfonylamino-2-sulfamoyl-phenyl)-malonamic acid methyl ester (V)

Original Synthetic Route

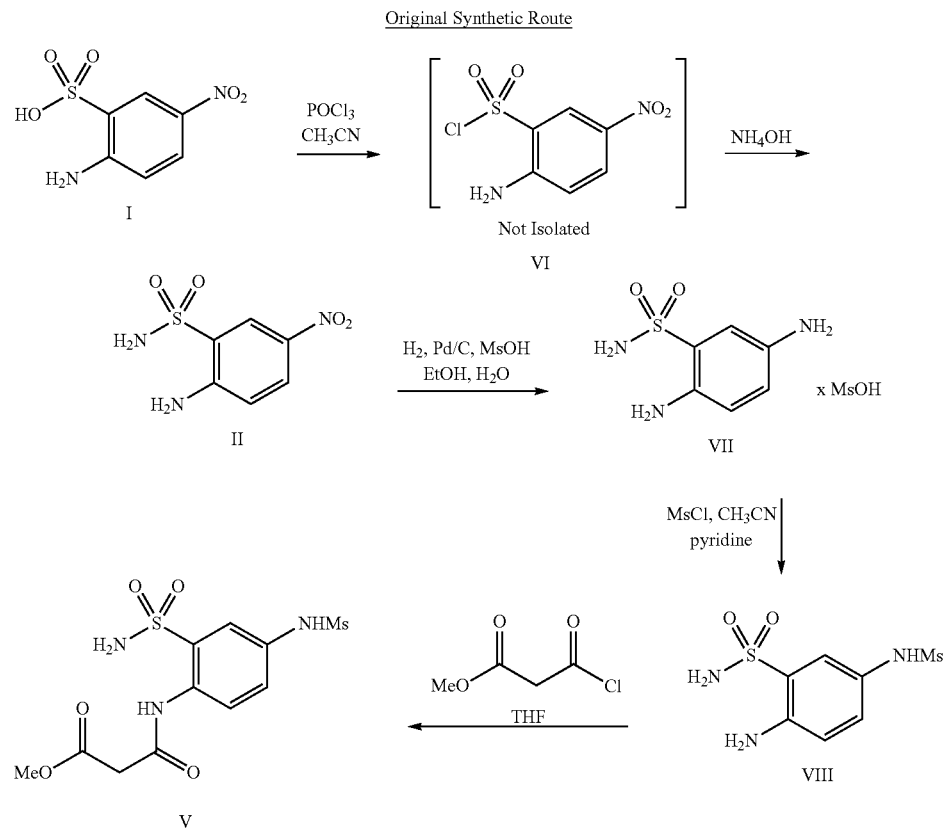

The present invention relates to a novel alternative preparation method for the key intermediate N-(4-methanesulfonylamino-2-sulfamoyl-phenyl)-malonamic acid methyl ester (V), which is useful in methods for the production of N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1λ$^6$,2,4-benzothiadiazin-7-yl)

In this previously described route to the key intermediate N-(4-methanesulfonylamino-2-sulfamoyl-phenyl)-malonamic acid methyl ester (V) for the production of Setrobuvir, the starting material, 2-amino-5-nitrobenzenesulfonic acid is first converted to the sulfonyl chloride with phosphorus oxychloride, and then quenched with aqueous ammonia, resulting in product (II). Hydrogenation of the nitrosulfonamide product in aqueous ethanol in the presence of methane sulfonic acid using palladium on carbon catalyst provides the mesylate salt of the 2,5-diamino-benzenesulfonamide. This salt is converted to the methanesulfonamide (VIII) with methanesulfonyl chloride and pyridine in acetonitrile. Finally reaction with methyl 3-chloro-3-oxopropanoate in THF provides the key intermediate N-(4-methanesulfonylamino-2-sulfamoyl-phenyl)-malonamic acid methyl ester (V).

lamino-benzenesulfonamide or it can cause color issues in Setrobuvir. The second advantage, and novel difference, is that the new route eliminates a chloro impurity that has been detected by LC/MS in (V) prepared by the original route.

In a preferred embodiment of the invention, the method for preparing the compound N-(4-methanesulfonylamino-2-sulfamoyl-phenyl)-malonamic acid methyl ester (V) comprises:

New Synthetic Route

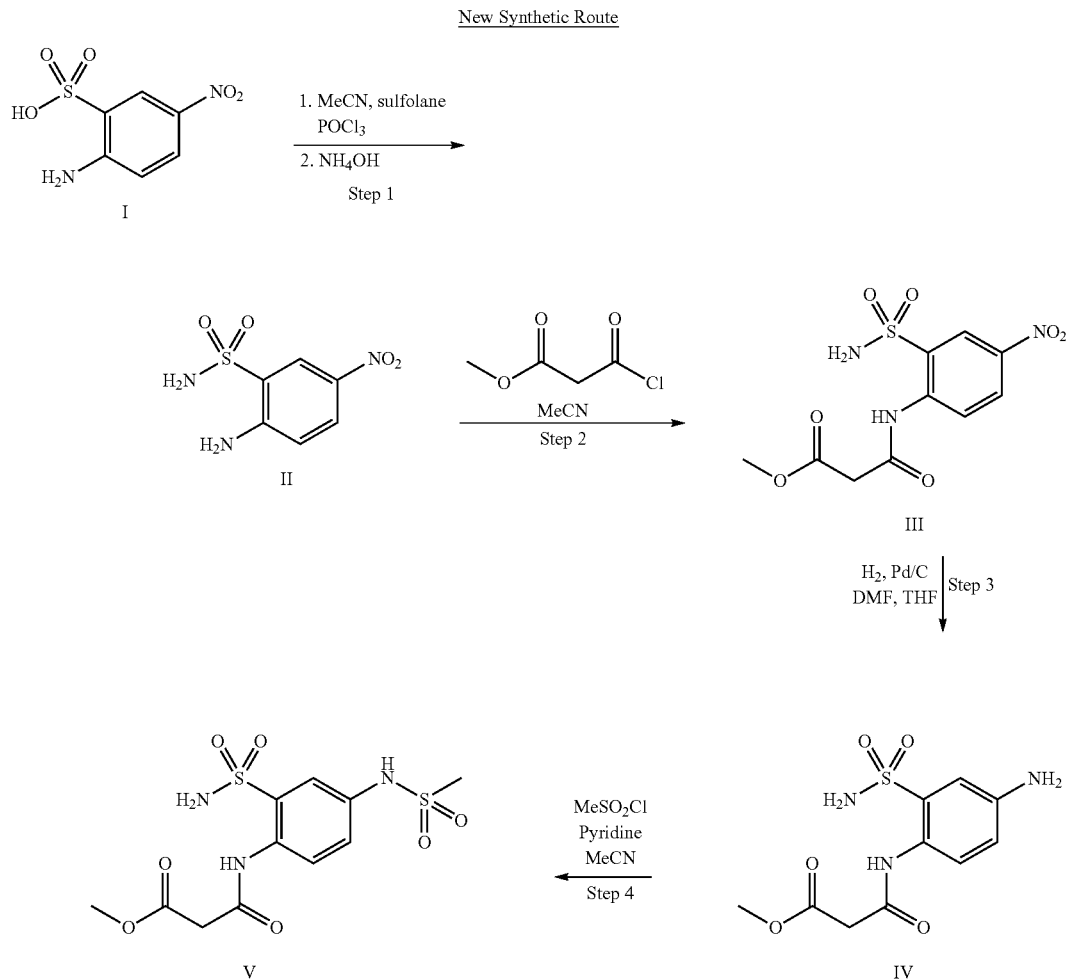

In the new route the order of the function group incorporation for the last 3 steps is changed. The first intermediate, 2-amino-5-nitrobenzenesulfonamide (II) is common to both routes. This intermediate is treated with methyl 3-chloro-3-oxopropanoate in acetonitrile. The nitro group is then reduced using hydrogen and palladium on carbon catalyst in a mixture of THF/DMF. Finally mesylation in acetonitrile using methanesulfonyl chloride and pyridine as the base provides the key intermediate N-(4-methanesulfonylamino-2-sulfamoyl-phenyl)-malonamic acid methyl ester (V).

There are two major and novel advantages for the new route over the method of making the key intermediate N-(4-methanesulfonylamino-2-sulfamoyl-phenyl)-malonamic acid methyl ester as disclosed in WO 2010/42834. The first advantage, and novel difference, is that the new route avoids the diaminobenzene intermediate (VII). This electron rich intermediate is prone to color generation which has to be reduced at the next intermediate 2-amino-5-methanesulfony- Step 1: Sulfonamide Formation A) Adding phosphorus oxychloride to a suspension of 2-amino-5-nitrobenzenesulfonic acid (I) in acetonitrile or a mixture of acetonitrile and sulfolane
B) Stirring the mixture under heat, preferably at 75-80° C. for 3-5 h, and then the supernatant was slowly transferred to a basic solution, preferably $NH_4OH$ (aqueous ammonia) solution, at less than 30° C., preferably at ambient room temperature
C) Concentrating and cooling the mixture to obtain 2-amino-5-nitro-benzenesulfonamide (II)

Step 2: Acylation
A) Suspending the 2-amino-5-nitrobenzenesulfonamide (II) in acetonitrile, and adding to this suspension methyl 3-chloro-3-oxopropanoate at ambient temperature until complete conversion is obtained (ca. 24 h). It is critical that this step is conducted in the absence of any added base to avoid decomposition of methyl 3-chloro-3-oxopropanoate as well as formation of the bis-acylation product.

B) Water is added, followed by a basic compound such as saturated aqueous sodium carbonate or sodium bicarbonate, to adjust the pH to about 7. More strongly basic compounds which can lead to more basic conditions, e.g. pH greater than 9, can lead to formation of side products such as the bis-acylation product as well as other cyclized (and decarboxylated) compounds.

C) Filtering and concentrating the filtrate to obtain N-(4-nitro-2-sulfamoyl-phenyl)-malonamic acid methyl ester (III).

Step 3—Catalytic Hydrogenation-Nitro-Reduction

A) Charging a reactor with a catalyst, preferably charging with palladium on carbon catalyst followed by a solution of N-(4-nitro-2-sulfamoyl-phenyl)-malonamic acid methyl ester (also known as methyl 3-(4-nitro-2-sulfamoylphenylamino)-3-oxopropanoate) (III) in a polar aprotic solvent, preferably a polar aprotic solvent mixture such as THF/DMF. It is important that a polar aprotic solvent such as, for example, DMF is required to keep the product N-(4-nitro-2-sulfamoyl-phenyl)-malonamic acid methyl ester in solution. Use of other polar (protic) solvents, such as IPA (isopropyl alcohol) and EtOH (ethanol), results in precipitation of the methyl 3-(4-amino-2-sulfamoylphenylamino)-3-oxopropanoate.

B) Hydrogenation of the N-(4-nitro-2-sulfamoyl-phenyl)-malonamic acid methyl ester in solution via pressuring the vessel with hydrogen gas, after nitrogen gas inertion, to complete conversion.

C) After complete conversion, filtering and concentrating the filtrate to obtain the product N-(4-amino-2-sulfamoyl-phenyl)-malonamic acid methyl ester (IV).

Step 4—Mesylation

A) Adding methanesulfonyl chloride to a suspension of N-(4-amino-2-sulfamoyl-phenyl)-malonamic acid methyl ester (also known as methyl 3-(4-amino-2-sulfamoylphenylamino)-3-oxopropanoate) (IV) and pyridine in acetonitrile at about 22-30° C., to obtain a mixture and stirring the mixture at ambient temperature until complete mesylation conversion occurs.

B) Upon complete conversion, water and brine are subsequently added. Following separation of the phases, the aqueous layer is extracted with acetonitrile or THF. Preferred method of aqueous layer extraction is with acetonitrile.

C) The combined organic layer are washed with brine, then concentrated to a slurry.

D) The solids from the slurry are filtered and washed with water to obtain the key intermediate N-(4-methanesulfonylamino-2-sulfamoyl-phenyl)-malonamic acid methyl ester (V).

The described synthetic pathways and experimental procedures utilize many common chemical abbreviations, known to those skilled in the art.

The new synthetic route provides a novel method that can be used to prepare the key intermediate N-(4-methanesulfonylamino-2-sulfamoyl-phenyl)-malonamic acid methyl ester (V), as well as the novel intermediate compounds of the present invention.

Experimental Section

The present compounds and method of the present invention will be further illustrated in the following example. The example is presented for purposes of demonstrating, but not limiting, the preparation of the key intermediate N-(4-methanesulfonylamino-2-sulfamoyl-phenyl)-malonamic acid methyl ester (V), used in the preparation of Setrobuvir, of the invention and the novel intermediate compounds of the invention.

Unless otherwise stated, the "%" used in the examples refers to weight percentage.

In accordance with the present invention, the following example is provided to illustrate a method for preparing compounds N-(4-nitro-2-sulfamoyl-phenyl)-malonamic acid methyl ester (also known as methyl 3-(4-nitro-2-sulfamoylphenylamino)-3-oxopropanoate) (III) and N-(4-amino-2-sulfamoyl-phenyl)-malonamic acid methyl ester (also known as methyl 3-(4-amino-2-sulfamoylphenylamino)-3-oxopropanoate) (IV), which are novel intermediates for the preparation of the key intermediate N-(4-methanesulfonylamino-2-sulfamoyl-phenyl)-malonamic acid methyl ester (V), which can be used for the preparation of the compound N-(3-{(1R,2S,7R,8S)-3-[(4-fluorophenyl)methyl]-6-hydroxy-4-oxo-3-azatricyclo[6.2.1.0$^{2,7}$]undec-5-en-5-yl}-1,1-dioxo-1,4-dihydro-1λ$^6$,2,4-benzothiadiazin-7-yl)methanesulfonamide (Setrobuvir).

Step 1: Sulfonamide Formation

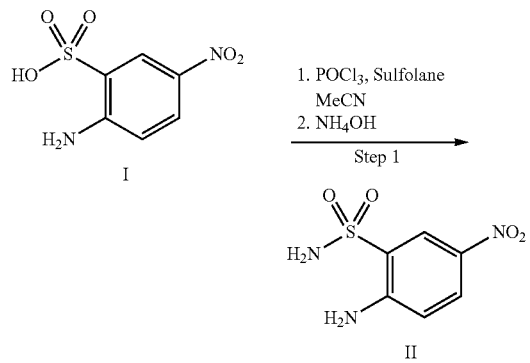

1. Phosphorus oxychloride (316 g, 192 mL, 2.06 mol, 1.8 equivalents) was slowly added to a suspension of 2-amino-5-nitrobenzenesulfonic acid (250 g, 1.15 mol, 1.00 equivalent) in a mixture of acetonitrile (2.54 kg, 2.0 L, 8 vol) and sulfolane (254 g, 200 mL, 0.8 vol) at ambient temperature.

2. This mixture was stirred at 75-80° C. for 3-5 h, and then the supernatant was slowly transferred to NH$_4$OH solution (28-30%, 1.5 L, 6 vol) such that the temperature was maintained below 30° C.

3. The reaction mixture was stirred at ambient temperature ca. 2 h, and was then concentrated under reduced pressure at ca. 50° C. to a minimum volume to obtain a slurry.

4. This slurry was aged at ca. 50° C. for ca. 2 h and then slowly cooled to ca. 10° C. and aged at ca. 10° C. for ca. 2 h. The solid was filtered and washed with water (3×250 mL, 3×1 vol) to give a yellow product which was dried at ca. 50° C. under vacuum for 2 days to yield 203.8 g of II (2-amino-5-nitro-benzenesulfonamide, See also compound described in Dragovich, P. S.; Thompson, P. A; Reubsam, F. WO 2010/042834, herein incorporated by reference in its entirety) in 81.9% yield with 99.0% purity by AN HPLC (area normalized high performance liquid chromatography).

Step 2: Acylation

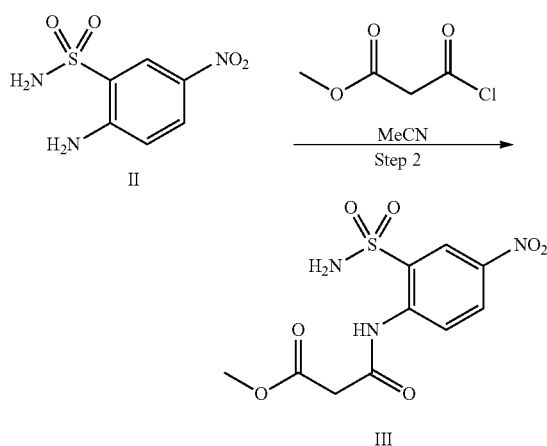

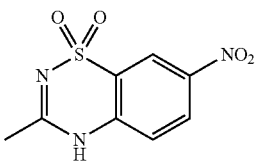

1. Methyl 3-chloro-3-oxopropanoate (163 g, 128 mL, 1.16 mol, 97% pure, 1.2 equivalents) was added to a suspension of 2-amino-5-nitrobenzenesulfonamide (210 g, 967 mmol, 1.00 equivalents) in acetonitrile (2.1 L, 10 vol) at ambient temperature and the mixture so obtained was stirred at ambient temperature until complete conversion was obtained (ca. 24 h). It is critical that this transformation is conducted in the absence of any base to avoid decomposition of methyl 3-chloro-3-oxopropanoate as well as formation of the bis-acylation product.

2. Water (210 mL, 1 vol) was added, followed by saturated aqueous sodium carbonate (336 mL, ca. 1.6 vol) to adjust the pH to ca. 7. The layers were separated and filtered through a pad of Celite. Note that the choice of base, i.e. aqueous $Na_2CO_3$, for pH adjustment was found to be important as stronger bases led to formation of side products such as the bis-acylation product as well as the cyclized (and decarboxylated) compounds shown below.

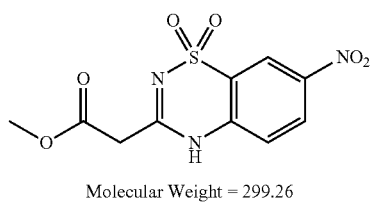 [SMILES: COC(=O)CC1=NS(=O)(=O)c2cc([N+](=O)[O-])ccc2N1]

Molecular Weight = 299.26

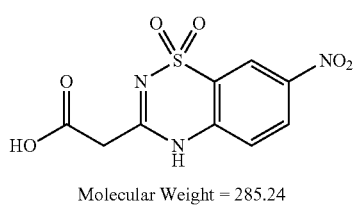 [SMILES: O=C(O)CC1=NS(=O)(=O)c2cc([N+](=O)[O-])ccc2N1]

Molecular Weight = 285.24

Molecular Weight = 241.23

3. The filtrate was concentrated under vacuum at ca. 40° C. to approximately half the volume to precipitate the product. Additional water (940 mL, 4.5 vol) was added and the distillation was continued under vacuum until no distillate was observed. The resulting slurry so obtained was stirred at ca. 40° C. for at least 1 h and then allowed to cool to ambient temperature.

4. The solids were filtered and washed with water (4×210 mL, 4×1 vol). The wet cake was dried in a vacuum oven at ca. 50° C. for ca. 18 h to obtain 286.8 g of product III (N-(4-nitro-2-sulfamoyl-phenyl)-malonamic acid methyl ester), 93.5% yield, 95.8% AN HPLC purity).

$^1$H NMR (300 MHz, DMSO-$d_6$) δ ppm 9.90 (br. s., 1H), 8.64 (dd, J=0.8, 2.2 Hz, 1H), 8.54-8.38 (m, 2H), 8.00 (br. s., 2H), 3.74 (s, 2H), 3.70 (s, 3H).

LC/MS m/z: (M+H)$^+$ 318.

Step 3: Catalytic Hydrogenation-Nitro-Reduction

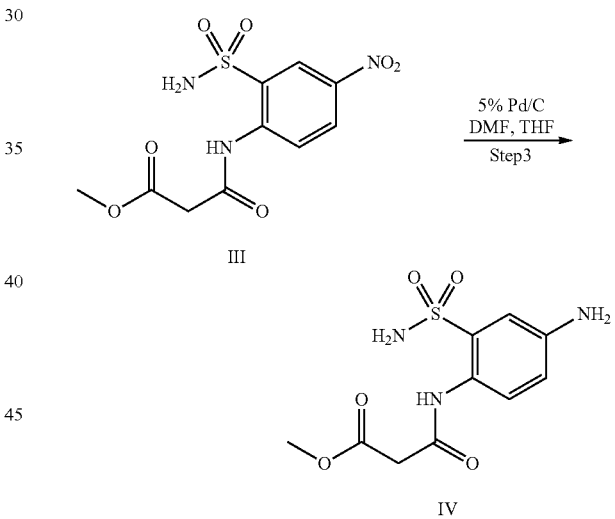

1. A 4-L Parr reactor was charged with palladium on carbon catalyst (5% Pd/C, 50% wet, 25 g) followed by a solution of N-(4-nitro-2-sulfamoyl-phenyl)-malonamic acid methyl ester (250 g) in 13:3 THF/DMF mixture (2.0 L, 8 vol). It is important that a polar aprotic solvent such as, for example, DMF (at least 2 volumes with respect to N-(4-nitro-2-sulfamoyl-phenyl)-malonamic acid methyl ester) is required to keep the product N-(4-nitro-2-sulfamoyl-phenyl)-malonamic acid methyl ester in solution.

2. The reaction vessel was inerted by pressurizing (3×) with nitrogen gas to ca. 100 psi. Hydrogen atmosphere in the vessel was established by pressurizing (3×) with hydrogen gas to ca. 200 psi, and finally the reaction mixture was pressurized to ca. 200 psi with hydrogen gas and heated to ca. 40° C. for 4-16 h with a stir rate of ca. 400 rpm.

3. Upon complete conversion (additional catalyst may be added), the reaction mixture was filtered through a pad of Celite to obtain a light yellow filtrate. The filtrate was concentrated under vacuum at ca. 40° C. to a minimum volume, to which was added IPA (1.25 L, 5 vol) to precipitate the product. The slurry so obtained was aged at ca. 40° C. for at least 30 min followed by addition of heptane (750 mL, 3 vol) and further aged at ca. 40° C. for an additional 2 h and then cooled slowly to ambient temperature.

4. The solids were filtered, washed with IPA/heptane mixture (4×250 mL, 4×1 vol) and dried under vacuum at ca. 60° C. for ca. 18 h to obtain 203.4 g of product IV (N-(4-amino-2-sulfamoyl-phenyl)-malonamic acid methyl ester), 89.9% yield and 98.7% AN HPLC purity).

$^1$H NMR (300 MHz, DMSO-$d_6$) δ ppm 9.17 (br. s., 1H), 7.35 (d, J=8.7 Hz, 1H), 7.18 (br. s., 2H), 7.10 (d, J=2.6 Hz, 1H), 6.71 (dd, J=2.6, 8.5 Hz, 1H), 5.48 (s, 2H), 3.67 (s, 3H), 3.52 (s, 2H).

LC/MS m/z: (M+H)$^+$ 288.

Step 4: Mesylation

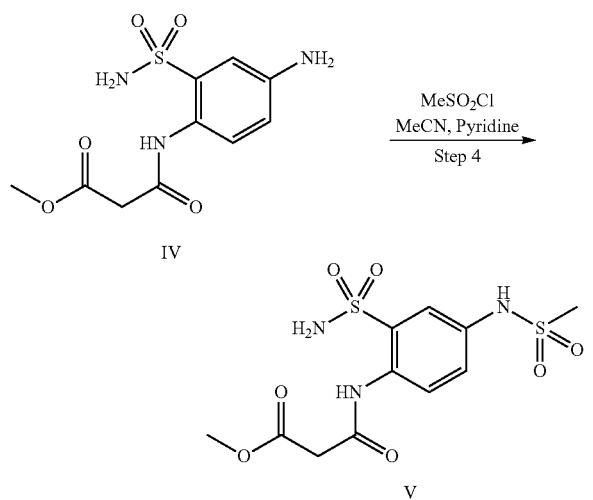

1. Methanesulfonyl chloride (95.7 g, 651 mL, 1.2 equivalents) was added to a suspension of N-(4-amino-2-sulfamoyl-phenyl)-malonamic acid methyl ester (200 g, 696 mmol, 1.0 equivalents) and pyridine (110 g, 113 ml, 1.39 mol, 2 equivalents) in acetonitrile (2.0 L, 10 vol) at 22-30° C. and the mixture so obtained was stirred at ambient temperature (30-60 min).

2. Upon complete conversion, water (400 mL, 2 vol) was added followed by 400 mL (2 vol) of brine. This mixture was stirred for ca. 15 min and then the phases were allowed to separate. The aqueous layer was then extracted with acetonitrile (400 mL, 2 vol).

3. The combined organic layers were washed with brine (600 mL, 3 vol) and then concentrated under vacuum (100 mbar) at ca. 40° C. until precipitation was observed. The slurry was aged for at least 30 min, and then water (1.0 L, 5 vol) was slowly added to the slurry. The distillation was recommenced at 50 mbar until no distillate was observed.

4. The slurry so obtained was aged at ca. 40° C. for ca. 2 h and then allowed to cool to ambient temperature.

5. The solids were filtered and washed with water (3×200 mL, 3×1 vol) to obtain off-white to light yellow material, which was dried at 50-60° C. under vacuum for ca. 18 h to obtain 230.3 g of (V) the key intermediate N-(4-methanesulfonylamino-2-sulfamoyl-phenyl)-malonamic acid methyl ester in 90.5% yield and 98.3% AN HPLC purity.

The invention claimed is:

1. A method for preparing compound N-(4-methanesulfonylamino-2-sulfamoyl-phenyl)-malonamic acid methyl ester, comprising;
    a. reacting 2-amino-5-nitrobenzenesulfonic acid with phosphorus oxychloride to form 2-amino-5-nitrobenzenesulfonamide
    b. adding methyl 3-choloro-3-oxypropanoate to 2-amino-5-nitrobenzenesulfonamide, in the absence of any additional base, to form N-(4-nitro-2-sulfamoyl-phenyl)-malonamic acid methyl ester,
    c. reducing the N-(4-nitro-2-sulfamoyl-phenyl)-malonamic acid methyl ester, via a catalyst in the presence of an polar aprotic solvent, to form N-(4-amino-2-sulfamoyl-phenyl)-malonamic acid methyl ester, and
    d. mesylating the N-(4-amino-2-sulfamoyl-phenyl)-malonamic acid methyl ester, via addition of methanesulfonyl chloride to a suspension of N-(4-amino-2-sulfamoyl-phenyl)-malonamic acid methyl ester and pyridine to form the compound N-(4-methanesulfonylamino-2-sulfamoyl-phenyl)-malonamic acid methyl ester.

2. The method of claim 1, wherein step b) additionally comprises addition of water after mixture of the methyl 3-choloro-3-oxypropanoate with the 2-amino-5-nitrobenzenesulfonamide to adjust the pH to about 7.

3. The method of claim 1, wherein the polar aprotic solvent of step c) is selected from the group consisting of DMF, DMA, THF, NMP or polar aprotic solvent mixtures thereof.

4. A compound, which is N-(4-nitro-2-sulfamoyl-phenyl)-malonamic acid methyl ester.

5. A compound, which is N-(4-amino-2-sulfamoyl-phenyl)-malonamic acid methyl ester.

6. The compound of claim 4 for use as an intermediate in the preparation of compound N-(4-methanesulfonylamino-2-sulfamoyl-phenyl)-malonamic acid methyl ester.

7. The compound of claim 5 for use as an intermediate in the preparation of compound N-(4-methanesulfonylamino-2-sulfamoyl-phenyl)-malonamic acid methyl ester.

* * * * *